(12) United States Patent
Hirota et al.

(10) Patent No.: US 10,174,359 B2
(45) Date of Patent: Jan. 8, 2019

(54) FLUORESCENT SEPARASE ACTIVITY SENSOR

(71) Applicant: JAPANESE FOUNDATION FOR CANCER RESEARCH, Tokyo (JP)

(72) Inventors: Toru Hirota, Tokyo (JP); Norihisa Shindo, Tokyo (JP); Kazuki Kumada, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 358 days.

(21) Appl. No.: 14/413,760

(22) PCT Filed: Jul. 10, 2013

(86) PCT No.: PCT/JP2013/068894
§ 371 (c)(1),
(2) Date: Jan. 9, 2015

(87) PCT Pub. No.: WO2014/010635
PCT Pub. Date: Jan. 16, 2014

(65) Prior Publication Data
US 2015/0140590 A1     May 21, 2015

Related U.S. Application Data

(60) Provisional application No. 61/670,306, filed on Jul. 11, 2012.

(51) Int. Cl.
| | | |
|---|---|---|
| *C12Q 1/37* | (2006.01) | |
| *G01N 33/50* | (2006.01) | |
| *G01N 33/542* | (2006.01) | |
| *C12N 9/64* | (2006.01) | |

(52) U.S. Cl.
CPC .............. *C12Q 1/37* (2013.01); *C12N 9/6472* (2013.01); *C12Y 304/22049* (2013.01); *G01N 33/5011* (2013.01); *G01N 33/542* (2013.01); *C07K 2319/01* (2013.01); *C07K 2319/50* (2013.01); *C07K 2319/60* (2013.01); *G01N 2333/96466* (2013.01); *G01N 2500/04* (2013.01)

(58) Field of Classification Search
None
See application file for complete search history.

(56) References Cited

FOREIGN PATENT DOCUMENTS

WO     02/057566 A2     7/2002

OTHER PUBLICATIONS

Chaing et al, Age-Dependent Susceptibility of Chromosome Cohesion to Premature Separase Activation in Mouse Oocytes. Biology of Reproduction 85, 1279-1283 (2011) Published online before print Aug. 24, 2011.*
Basu et al, Development and validation of a fluorogenic assay to measure separase enzyme activity. Analytical Biochemistry 392 (2009) 133-138.*
Ibraheem et al, Designs and applications of fluorescent protein-based biosensors. Current Opinion in Chemical Biology 2010, 14:30-36.*
Shelby et al, Dynamic Elastic Behavior of αL-Satellite DNA Domains Visualized In Situ in Living Human Cells. The Journal of Cell Biology, vol. 135, No. 3, Nov. 1996 545-557.*
UniProt ID# RAD21_HUMAN from Hauf et al, Cohesin cleavage by separase required for anaphase and cytokinesis in human cells. Science 293:1320-1323(2001). Alignment with SID1.*
McIntyre et al, In vivo analysis of cohesin architecture using FRET in the budding yeast *Saccharomyces cerevisiae*. The EMBO Journal (2007) 26, 3783-3793.*
McIntyre et al, In vivo analysis of cohesin architecture using FRET in the budding yeast *Saccharomyces cerevisiae*. The EMBO Journal (2007) 26, Suppplementary Info. 6 pages.*
Horihisa Shindo and Toru Hirota, "Mechanism of cell division— visualizing the activity of separase and Jeciphering its regulation", Bioscience & Industry, vol. 71, No. 3, pp. 229-233, (Jan. 5, 2013), listed in International Search Report, English abstract included.*
International Search Report, dated Oct. 8, 2013 (Oct. 8, 2013).
Raquel A. Oliveira and Kim Nasmyth, "Getting through anaphase: splitting the sisters and beyond", Chromosome Segregation and Aneuploidy, Jun. 19-23, 2010, Edinburgh, U.K., vol. 38, Part 6, pp. 1639-1644, discussed in specification, English text.
Frank Uhlmann et al., "Cleavage of Cohesin by the CD Clan Protease Separin Triggers Anaphase in Yeast", Cell, vol. 103, pp. 375-386, Oct. 27, 2000, Copyright 2000 by Cell Press, discussed in specification, English text.
Hironori Funabiki et al. "Fission yeast Cut1 and Cut2 are essential for sister chromatid separation, concentrate along the metaphase spindle and form large complexes", The EMBO Journal vol. 15, No. 23, pp. 6617-6628, 1996, Oxford University Press, discussed in specification, English text.
Rafal Ciosk et al., "An ESP1/PDS1 Complex Regulates Loss of Sister Chromatid Cohesion at the Metaphase to Anaphase Transition in Yeast", Cell, vol. 93, pp. 1067-1076, Jun. 12, 1988, Copyright 1998 by Cell Press, discussed in specification, English text.
Hui Zou et al. "Identification of a Vertebrate Sister-Chromatid Separation Inhibitor Involved in Transformation and Tumorigenesis", Science vol. 285, pp. 418-422, Jul. 16, 1999, discussed in specification, English text.

(Continued)

Primary Examiner — Sheridan Swope
(74) Attorney, Agent, or Firm — Rankin, Hill & Clark LLP

(57) ABSTRACT

Problem to be Solved
An object of the present invention is to provide a separase sensor for visualizing separase activity in a living cell. Another object is to develop a function analysis system of cell division using the separase sensor and further obtain a simple screening method for an anticancer agent.
Solution
The separase sensor of the present invention has two types of fluorescent proteins different in fluorescence wavelength at both ends of an amino acid sequence containing a separase cleavage site and a localization-targeting sequence targeting to a specific site within a cell. Since timing of activating separase and location of separase in a cell can be specified by use of the sensor, cell division can be analyzed and an anticancer agent can be screened.

10 Claims, 8 Drawing Sheets

Specification includes a Sequence Listing.

(56) References Cited

OTHER PUBLICATIONS

Gregory C. Rogers et al., "Two mitotic kinesins cooperate to drive sister chromatid separation during anaphase", Nature, Nature Publishing Group, vol. 427, pp. 364-370, Jan. 22, 2004, discussed in specification, English text.
Frank Wolf et al., "Dose-dependent effects of stable cyclin B1 on progression through mitosis in human cells", The EMBO Journal (2006) vol. 25, No. 12, pp. 2802-2813, discussed in specification, English text.
Toru Higuchi & Frank Uhlmann, "Stabilization of microtubule dynamics at anaphase onset promotes chromosome segregation", Nature Publishing Group, Nature, vol. 433, pp. 171-176, Jan. 13, 2005, discussed in specification, English text.
Raquel A. Oliveira et al., "Cohesin cleavage and Cdk inhibition trigger formation of daughter nuclei", Macmillan Publishers Limited, Nature Cell Biology, vol. 12, No. 2, pp. 185-192, Feb. 2010, discussed in specification, English text.
Silke Hauf et al., "Cohesin Cleavage by Separase Required for Anaphase and Cytokinesis in Human Cells", Science, vol. 293, pp. 1320-1323, Aug. 17, 2001, discussed in specification, English text.
Catherine T. Sigal et al., "Amino-terminal basic residues of Src mediate membrane binding through electrostatic interaction with acidic phospholipids", Proc. Natl. Acad. Sci. USA, vol. 91, pp. 12253-12257, Dec. 1994 Biochemistry, discussed in specification, English text.
Michael M. Kessels and Britta Qualmann, "Syndapins integrate N-WASP in receptor-mediated endocytosis", The EMBO Journal, vol. 21, No. 22, pp. 6083-6094, 2002, discussed in specification, English text.
Nadine CD Hornig and Frank Uhlmann, "Preferential cleavage of chromatin-bound cohesin after targeted phosphorylation by Polo-like kinase", The EMBO Journal (2004), vol. 23, No. 15, pp. 3144-3153, discussed in specification, English text.
Yuxiao Sun et al., "Separase Is Recruited to Mitotic Chromosomes to Dissolve Sister Chromatid Cohesion in a DNA-Dependent Manner", Cell vol. 137, pp. 123-132, Apr. 3, 2009, Elsevier Inc., discussed in specification, English text.
Silke Hauf et al., "The small molecule Hesperadin reveals a role for Aurora B in correcting kinetochore-microtubule attachment and in maintaining the spindle assembly checkpoint", The Rockefeller University Press, vol. 161, No. 2, pp. 281-294, Apr. 28, 2003, discussed in specification, English text.
Claire Ditchfield et al., "Aurora B couples chromosome alignment with anaphase by targeting BubR1, Mad2, and Cenp-E to kinetochores", The Rockefeller University Press, vol. 161, No. 2, pp. 267-280, Apr. 28, 2003, discussed in specification, English text.
Prasad V. Jallepalli et al., "Securin is Required for Chromosomal Stability in Human Cells", Cell, vol. 105, pp. 445-457, May 18, 2001, Copyright 2001 by Cell Press, discussed in specification, English text.
Junjie Mei et al., "Securin is not required for cellular viability, but is required for normal growth of mouse embryonic fibroblasts", Current Biology, vol. 11, No. 15, pp. 1197-1201 (2001), discussed in specification, English text.
Zhiyong Wang et al., "Mice Lacking Pituitary Tumor Transforming Gene Show Testicular and Splenic Hypoplasia, Thymic Hyperplasia, Thrombocytopenia, Aberrant Cell Cycle Progression, and Premature Centromere Division", Molecular Endocrinology, vol. 15, No. 11, pp. 1870-1879, Nov. 2001, Copyright 2001 by the Endocrine Society, discussed in specification, English text.
Katrin Pfleghaar et al., "Securin is Not Required for Chromosomal Stability in Human Cells", PLoS Biology, vol. 3, Issue 12, pp. 2127-2134, Dec. 2005, discussed in specification, English text.
Olaf Stemmann et al., "Dual Inhibition of Sister Chromatid Separation at Metaphase", Cell, vol. 107, pp. 715-726, Dec. 14, 2001, Copyright 2001 by Cell Press, discussed in specification, English text.
Ingo H. Gorr et al., "Mutual Inhibition of Separase and Cdk1 by Two-Step Complex Formation", Molecular Cell, vol. 19, 135-141, Jul. 1, 2005, Copyright 2005 by Elsevier Inc., discussed in specification, English text.
Xingxu Huang et al., "Securin and Separase Phosphorylation Act Redundantly to Maintain Sister Chromatid Cohesion in Mammalian Cells", Molecular Biology of the Cell, vol. 16, pp. 4725-4732, Oct. 2005, discussed in specification, English text.
Andrew J. Holland and Stephen S. Taylor, "Cyclin-B1-mediated inhibition of excess separase is required for timely chromosome disjunction", Journal of Cell Science, vol. 119, No. 16, pp. 3325-3336, May 30, 2006, discussed in specification, English text.
Ina Poser et al., "BAC TransgeneOmics: a high-throughput method for exploration of protein function in mammals", Natl Methods May 2008, vol. 5, No. 5, pp. 409-415, discussed in specification, English text.
Hui Zou et al., "Anaphase specific auto-cleavage of separase", FEBS Letters, vol. 528, pp. 246-250, Aug. 22, 2002, Published by Elsevier Science B.V., discussed in specification, English text.
Irene C. Waizenegger et al., "Regulation of Human Separase by Securin Binding and Autocleavage", Current Biology, vol. 12, pp. 1368-1378, Aug. 20, 2002, 2002 Elsevier Science Ltd., discussed in specification, English text.
Hidemasa Goto et al., "Complex formation of Plk1 and INCENP required for metaphase-anaphase transition", Nature Cell Biology, vol. 8, No. 2, pp. 180-187, Feb. 2006, discussed in specification, English text.
Dipanjan Basu et al., "Development and validation of a fluorogenic assay to measure separase enzyme activity", Analytical Biochemistry, vol. 392, No. 2, pp. 133-138, (Jun. 2, 2009), listed in International Search Report, English text.
Teresa Chiang et al., "Age-Dependent Susceptibility of Chromosome Cohesion to Premature Separase Activation in Mouse Oocytes", Biology of Reproduction, vol. 85, No. 6, pp. 1279-1283, (Aug. 24, 2011), listed in International Search Report, English text.
Brian G. Fuller et al., "Midzone activation of aurora B in anaphase produces an intracellular phosphorylation gradient", Nature, vol. 453, No. 7198, pp. 1132-1136, (May 7, 2008), listed in International Search Report, English text.
Norihisa Shindo et al., "Separase Sensor Reveals Dual Roles for Separase Coordinating Cohesin Cleavage and Cdk1 Inhibition", Developmental Cell, vol. 23, No. 1, pp. 112-123, Jul. 17, 2012, listed in International Search Report, English text.
Frank Uhlmann et al., "Sister-chromatid separation at anaphase onset is promoted by cleavage of the cohesin subunit Scc1", Nature, vol. 400, No. 6739, pp. 37-42, (Jul. 1, 1999), listed in International Search Report, English text.
Yaakov, et al. "Separase Biosensor Reveals that Cohesin Cleavage Timing Depends on Phosphatase PP2A Cdc55 Regulation", Cell Press, Developmental Cell Article 23, 124-138, Jul. 17, 2012, 14 pages.
Morihisa Shindo and Toru Hirota, "Mechanism of cell division—visualizing the activity of separase and deciphering its regulation", Bioscience & Industry, vol. 71, No. 3, pp. 229-233, (Jan. 5, 2013), listed in International Search Report, English abstract included.
Mitsuhiro Yanagida, "Clearing the way for mitosis: is cohesin a target?", Nature Reviews/Molecular Cell Biology, vol. 10, pp. 489-496, Jul. 2009, discussed in specification, English text.
International Search Report, dated Oct. 8, 2013 (Oct. 8, 2013), 2 pages.

\* cited by examiner wild-type      —DREIM RE——IE EPSRLQESVMEASRT— Seq.ID No. 1
non-cleavable  —DRRIM EE——IE RPSELQESVMRASET— Seq.ID No. 2

FIG.3C

SEQUENCE LISTING

```
<160> NUMBER OF SEQ ID NOS: 2

<210> SEQ ID NO 1
<211> LENGTH: 326
<212> TYPE: PRT
<213> ORGANISM: Homo sapiens

<400> SEQUENCE: 1

Glu Ile Thr Met Arg Glu Glu Val Gly Asn Ile Ser Ile Leu Gln Glu
1               5                   10                  15

Asn Asp Phe Gly Asp Phe Gly Met Asp Asp Arg Glu Ile Met Arg Glu
            20                  25                  30

Gly Ser Ala Phe Glu Asp Asp Met Leu Val Ser Thr Thr Thr Ser
        35                  40                  45

Asn Leu Leu Leu Glu Ser Glu Gln Ser Thr Ser Asn Leu Asn Glu Lys
    50                  55                  60

Ile Asn His Leu Glu Tyr Glu Asp Gln Tyr Lys Asp Asp Asn Phe Gly
65                  70                  75                  80

Glu Gly Asn Asp Gly Gly Ile Leu Asp Asp Lys Leu Ile Ser Asn Asn
                85                  90                  95

Asp Gly Gly Ile Phe Asp Asp Pro Pro Ala Leu Ser Glu Ala Gly Val
            100                 105                 110

Met Leu Pro Glu Gln Pro Ala His Asp Asp Met Asp Glu Asp Asp Asn
        115                 120                 125

Val Ser Met Gly Gly Pro Asp Ser Pro Asp Ser Val Asp Pro Val Glu
    130                 135                 140

Pro Met Pro Thr Met Thr Asp Gln Thr Thr Leu Val Pro Asn Glu Glu
```

```
                145                 150                 155                 160
        Glu Ala Phe Ala Leu Glu Pro Ile Asp Ile Thr Val Lys Glu Thr Lys
                        165                 170                 175

Ala Lys Arg Lys Arg Lys Leu Ile Val Asp Ser Val Lys Glu Leu Asp
                        180                 185                 190

Ser Lys Thr Ile Arg Ala Gln Leu Ser Asp Tyr Ser Asp Ile Val Thr
                        195                 200                 205

Thr Leu Asp Leu Ala Pro Pro Thr Lys Lys Leu Met Met Trp Lys Glu
                    210                 215                 220

Thr Gly Gly Val Glu Lys Leu Phe Ser Leu Pro Ala Gln Pro Leu Trp
        225                 230                 235                 240

Asn Asn Arg Leu Leu Lys Leu Phe Thr Arg Cys Leu Thr Pro Leu Val
                        245                 250                 255

Pro Glu Asp Leu Arg Lys Arg Arg Lys Gly Gly Glu Ala Asp Asn Leu
                        260                 265                 270

Asp Glu Phe Leu Lys Glu Phe Glu Asn Pro Glu Val Pro Arg Glu Asp
                        275                 280                 285

Gln Gln Gln Gln His Gln Gln Arg Asp Val Ile Asp Glu Pro Ile Ile
                    290                 295                 300

Glu Glu Pro Ser Arg Leu Gln Glu Ser Val Met Glu Ala Ser Arg Thr
        305                 310                 315                 320

Asn Ile Asp Glu Ser Ala
                        325

<210> SEQ ID NO 2
<211> LENGTH: 326
<212> TYPE: PRT
<213> ORGANISM: Homo sapiens

<400> SEQUENCE: 2

Glu Ile Thr Met Arg Glu Val Gly Asn Ile Ser Ile Leu Gln Glu
        1                   5                   10                  15

Asn Asp Phe Gly Asp Phe Gly Met Asp Asp Arg Arg Ile Met Glu Glu
                        20                  25                  30

Gly Ser Ala Phe Glu Asp Asp Met Leu Val Ser Thr Thr Thr Ser
                    35                  40                  45

Asn Leu Leu Leu Glu Ser Glu Gln Ser Thr Ser Asn Leu Asn Glu Lys
                50                  55                  60

Ile Asn His Leu Glu Tyr Glu Asp Gln Tyr Lys Asp Asn Phe Gly
        65                  70                  75                  80

Glu Gly Asn Asp Gly Gly Ile Leu Asp Lys Leu Ile Ser Asn Asn
                        85                  90                  95

Asp Gly Gly Ile Phe Asp Asp Pro Pro Ala Leu Ser Glu Ala Gly Val
                        100                 105                 110

Met Leu Pro Glu Gln Pro Ala His Asp Asp Met Asp Glu Asp Asn
                    115                 120                 125

Val Ser Met Gly Gly Pro Asp Ser Pro Asp Ser Val Asp Pro Val Glu
                130                 135                 140

Pro Met Pro Thr Met Thr Asp Gln Thr Thr Leu Val Pro Asn Glu Glu
        145                 150                 155                 160

Glu Ala Phe Ala Leu Glu Pro Ile Asp Ile Thr Val Lys Glu Thr Lys
                        165                 170                 175

Ala Lys Arg Lys Arg Lys Leu Ile Val Asp Ser Val Lys Glu Leu Asp
                        180                 185                 190
```

-continued

```
Ser Lys Thr Ile Arg Ala Gln Leu Ser Asp Tyr Ser Asp Ile Val Thr
        195                 200                 205

Thr Leu Asp Leu Ala Pro Pro Thr Lys Lys Leu Met Met Trp Lys Glu
        210                 215                 220

Thr Gly Gly Val Glu Lys Leu Phe Ser Leu Pro Ala Gln Pro Leu Trp
225                 230                 235                 240

Asn Asn Arg Leu Leu Lys Leu Phe Thr Arg Cys Leu Thr Pro Leu Val
                245                 250                 255

Pro Glu Asp Leu Arg Lys Arg Arg Lys Gly Gly Glu Ala Asp Asn Leu
            260                 265                 270

Asp Glu Phe Leu Lys Glu Phe Glu Asn Pro Glu Val Pro Arg Glu Asp
        275                 280                 285

Gln Gln Gln Gln His Gln Gln Arg Asp Val Ile Asp Glu Pro Ile Ile
        290                 295                 300

Glu Arg Pro Ser Glu Leu Gln Glu Ser Val Met Arg Ala Ser Glu Thr
305                 310                 315                 320

Asn Ile Asp Glu Ser Ala
                325
```

FLUORESCENT SEPARASE ACTIVITY SENSOR

TECHNICAL FIELD

The present invention relates to a biosensor that can visualize the activation of separase in vivo.

BACKGROUND ART

Cell division is a basic process for developing and growing living organisms, needless to say, which is the most dynamic behavior in a biological cell cycle. It is widely known that abnormal regulation of cell division leads to "malignant alteration". Cell division is a very important process but still many points remain unexplained. One of these points (riddles) is synchronized motion of chromosomes that momentarily occurs and observed in cell division.

It has been known for 100 years or more that the number of chromosomes of a cancer cell differs from that of a normal cell. It has been also known that the number of chromosomes of a cancer cell easily varies, and that cancer cells having different number of chromosomes are produced in a cancer-cell proliferation. Such variation in the number of chromosomes, in other words, chromosomal instability, contributes to diversity of cancer cells, furthermore, a high grade of malignancy. The diversity of cancer cells constituting a tumor is the biggest factor that makes it difficult to treat cancer. In other words, due to the presence of diversified cancer cells different in resistance to an anticancer agent, it difficult to kill all cancer cells.

From the above background, analyzing a molecular mechanism underlying chromosomal instability may lead to develop a new treatment of cancer. From the expectation, attention has been focused on importance of genes involved in cohesion or segregation of sister chromatids. In particular, overexpression of separase, which is a protease cleaving an adhesion factor called cohesin present between sister chromatids, and securin, which is a one of regulatory factor for separase, has been reported to cause chromosomal instability, leading to canceration of the cell. Overexpression of separase and securin is considered as a significant factor in the "malignant alteration" process.

Basically, in the progression process of a normal cell division, segregation of sister chromatids is an important event and strictly controlled. In the segregation of sister chromatids, two events, i.e., removal of cohesin and poleward movement of chromatids, are controlled to simultaneously proceed (Non Patent Literatures 1, 2).

The former is started when cohesin, a protein complex that holds sister chromatids together, is decomposed by the protease separase (Non Patent Literatures 3, 4). Separase is known to be activated by control of securin (Non Patent Literatures 5-7).

The latter involves proteins that regulate microtubule, including kinesins that promote microtubule depolymerization (Non Patent Literature 8), and chromokinesins (Non Patent Literature 9). Little is known about the mechanism that controls these proteins, but it is said that the mechanism depends on a decrease in cyclin-dependent kinase (Cdk1) activity (Non Patent Literatures 9-11).

It is considered that the two processes, i.e., removal of cohesin and poleward movement of chromosomes are cooperatively, orderly and strictly controlled, in consideration that all chromosomes segregate and move poleward in an extremely short time.

CITATION LIST

Non Patent Literatures

Non Patent Literature 1: Oliveira, R. A., and Nasmyth, K. (2010) Biochem. Soc. Trans., Vol. 38, p. 1639-1644
Non Patent Literature 2: Yanagida, M. (2009) Nat. Rev. Mol. Cell Biol., Vol. 10, p. 489-496
Non Patent Literature 3: Uhlmann, F., et al. (1999) Nature, Vol. 400, p. 37-42
Non Patent Literature 4: Uhlmann, F., et al. (2000) Cell, Vol. 103, p. 375-386
Non Patent Literature 5: Funabiki, H., et al. (1996) EMBO J., Vol. 15, p. 6617-6628
Non Patent Literature 6: Ciosk, R., et al. (1998) Cell, Vol. 93, p. 1067-1076
Non Patent Literature 7: Zou, H., et al. (1999) Science, vol. 285, p. 418-422
Non Patent Literature 8: Rogers, G. C., et al. (2004) Nature, Vol. 427, p. 364-370
Non Patent Literature 9: Wolf, F., et al. (2006) EMBO J., Vol. 25, p. 2802-2813
Non Patent Literature 10: Higuchi. T, and Uhlmann, F. (2005) Nature, Vol. 433, p. 171-176
Non Patent Literature 11: Oliveira, R. A., et al. (2010) Nat. Cell Biol., Vol. 12, p. 185-192
Non Patent Literature 12: Hauf, S., et al. (2001) Science, Vol. 293, p. 1320-1323
Non Patent Literature 13: Sigal, C. T., (1994) Proc. Natl. Acad. Sci. USA, Vol. 91, p. 12253-12257
Non Patent Literature 14: Kessels, M. M., and Qualmann, B. (2002) EMBO J., Vol. 21, p. 6083-6094
Non Patent Literature 15: Hornig, N. C. D., and Uhlmann, F. (2004) EMBO J., Vol. 23, p. 3144-3153
Non Patent Literature 16: Sun, Y., et al., (2009) Cell, Vol. 137, p. 123-132
Non Patent Literature 17: Hauf, S., et al., (2003) J. Cell Biol., Vol. 161, p. 281-294
Non Patent Literature 18: Ditchfield, C., et al., (2003) J. Cell Biol., Vol. 161, p. 267-280
Non Patent Literature 19: Jallepalli, P. V., et al., (2001) Cell, Vol. 105, p. 445-457
Non Patent Literature 20: Mei, J., et al., (2001) Curr. Biol., Vol. 11, p. 1197-1201
Non Patent Literature 21: Wang, Z., et al., (2001) Mol. Endocrinol., Vol. 15, p. 1870-18790
Non Patent Literature 22: Pfleghaar, K., et al., (2005) PLoS Biol Vol. 3, e416
Non Patent Literature 23: Stemmann, O., et al., (2001). Cell, Vol. 107, p. 715-726
Non Patent Literature 24: Gorr, I. H. et al., (2005) Mol. Cell, Vol. 19, p. 135-141
Non Patent Literature 25: Huang, X., et al., (2005) Mol. Biol. Cell, Vol. 16, p. 4725-4732
Non Patent Literature 26: Holland, A. J. and Taylor, S. S. (2006) J. Cell Sci., Vol. 119, p. 3325-3336
Non Patent Literature 27: Poser, L., et al., (2008) Nat. Methods Vol. 5, p. 409-415
Non Patent Literature 28: Zou, H. et al., (2002) FEBS Lett. Vol. 528, p. 246-250
Non Patent Literature 29: Waizenegger, I., et al., (2002) Curr. Biol. Vol. 12, p. 1368-1378

Non Patent Literature 30: Goto, H. K., et al., (2006) Nat. Cell Biol. Vol. 8, p. 180-187

SUMMARY OF INVENTION

Technical Problem

How to control and proceed a chromosomal segregation process strictly synchronized has not yet been utterly elucidated. A key for elucidating the chromosomal segregation process is conceivably understanding a mechanism of controlling separase, which breaks junction of sister chromatids; however, timing of activating separase has not so far been elucidated. In the cell division process, which cooperatively proceeds in a short time of only 60 seconds, it is extremely difficult to biochemically analyze the timing of activating separase.

Mechanism of activating separase has not long been elucidated. It is still unclear when and where in the cell division process, separase is activated. If in-vivo behavior of separase including its mechanism and timing of activation is elucidated, pathologic conditions of a cell such as chromosomal instability found in a cancer cell, pathologic conditions in connection with malignant transformation of cancer such as metastasis and infiltration, and a clue to finding therapeutic strategy may successfully be found.

An object of the present invention is to provide a biosensor, which visualizes separase activity in living cells. If the activation of separase can be visualized in the living cell to be divided, timing of separase activation and location of separase within the cell can be elucidated. Another object of the present invention is to elucidate a mechanism which enables short-time chromosomal segregation, thereby obtaining a screening method for an anticancer agent.

Solution to Problem

The separase sensor of the present invention for visualizing separase activity has two types of fluorescent substances different in fluorescence wavelength at both ends of a amino acid sequence containing a separase cleavage site and a localization-targeting sequence.

The separase sensor of the present invention has a localization-targeting sequence, which is designed to instruct the sensor to locate in a predetermined site within a cell such as chromosome. Two types of fluorescent substances are arranged at both ends of the cleavage site of separase. Since the sensor is separated at the cleavage site upon activation of separase, activation of separase can be determined based on extinction of light from one of the fluorescent substances as an index.

The separase sensor of the present invention has a partial sequence at positions 142 to 467 of the amino acid sequence of human Scc1 including the separase cleavage site, as a pseudo substrate.

Owing to use of the sequence, i.e., a partial sequence of Scc1, serving as a substrate of separase, activation of separase can be sensitively determined.

Since the partial sequence of Scc1 includes two separase cleavage sites and serves as a pseudo substrate satisfactorily recognized by separase and cleaved, a highly sensitive separase sensor can be constructed.

In the separase sensor of the present invention, the fluorescent substances are fluorescent proteins.

Owing to use of fluorescent proteins, a sensor labeled with two types of fluorescent proteins can be prepared without labeling with fluorescent dyes.

In the separase sensor of the present invention, the localization-targeting sequence is a sequence targeting localization of the sensor in centromere, chromosome, cytoplasmic membrane or mitochondria.

If the sensor is localized in centromere, chromosome, cytoplasmic membrane or mitochondria within a cell, it is possible to specify where separase is activated.

In the separase sensor of the present invention, the localization-targeting sequence is a sequence targeting localization in centromere or chromosome, more specifically, is CENP-B or histone H2B.

Since separase has an important role in chromosomal segregation, a fusion protein is designed by adding CENP-B for localization in centromere and histone H2B for localization in chromosome, as the localization-targeting sequence.

Owing to this, the separase sensor of the present invention is allowed to localize in centromere or chromosome. Thus, the timing of separase activation in centromere or chromosome and the position of chromosome where separase is activated can be sensitively observed.

A method for analyzing a chromosomal segregation mechanism of the present invention includes expressing an expression vector for expressing the separase sensor within a cell, and visualizing separase activity in a living cell.

A localization-targeting sequence and a separase cleavage site sandwiched between two types of fluorescent proteins are fused and the fusion protein is integrated into an expression vector and the vector is allowed to express within a cell. In this manner, activation of separase can be simply and sensitively visualized.

A method for screening an anticancer agent of the present invention includes introducing an expression vector for expressing the separase sensor into a cell and administering a test substance to visualize the separase activity at a cell level, thereby screening an anticancer agent targeting a separase molecule based on the separase activity serving an index.

Chromosomal instability is a pathologic condition of a cancer cell itself and involved in malignant transformation of cancer, such as metastasis and infiltration; however, an anticancer agent targeting a separase molecule has not so far been developed. The separase sensor of the present invention can sensitively visualize and analyze the activation of separase. Therefore, in order to obtain an anticancer agent targeting a separase molecule, it can be expected to use the separase sensor for screening compounds.

BRIEF DESCRIPTION OF DRAWINGS

FIG. 3C is a graph showing relative protein amounts of individual fractions as described in Example 2.

DESCRIPTION OF EMBODIMENTS

The present invention will be more specifically described by way of Examples, below.

Example 1

(Preparation of Fluorescent Sensor for Analyzing Activation Profile of Separase)

To analyze the timing of separase activation, a fluorescence-based sensor that enables the detection of separase activity at a single-cell level was developed.

To the N terminal of a Scc1 polypeptide containing a separase cleavage site, EGFP emitting green fluorescence was added. To the C terminal of the polypeptide, mCherry emitting red fluorescence was added. In this manner, a fusion protein (FIG. 1) to be expressed was prepared.

Figure 1:
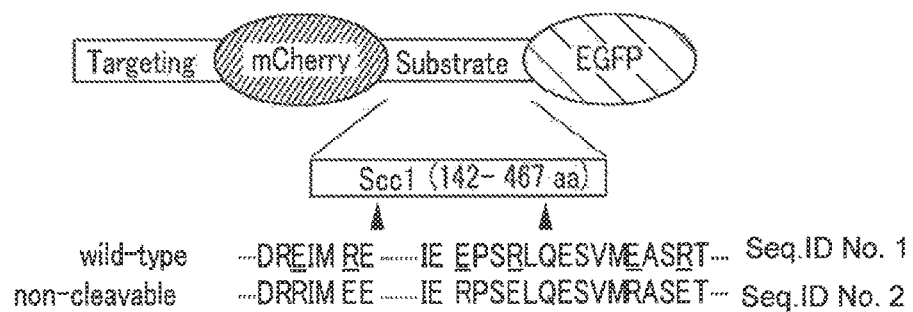
FIG. 1 shows design of a separase sensor.

As Scc1, which is used as a pseudo substrate of the separase sensor, an amino acid sequence of separase corresponding to 142nd to 467th (wild-type) thereof and containing two separase cleavage sites is used (SEQ ID NO. 1). In accordance with the report (Non Patent Literature 12) by Hauf et al., the non-cleavable site (not cleaved by separase) of Scc1 of a control sensor (non-cleavable) was prepared by replacing arginine with glutamic acid and glutamic acid with arginine (underlined as shown in FIG. 1, (SEQ ID NO. 2). Note that full length Scc1 cannot be used as a sensor since its expression amount is extremely low (data is not shown). It is also noted that it is known that a partial sequence of Scc1 containing only a single cleavage site is not cleaved.

The localization-targeting sequences used herein are as follow: human CENP-B (full-length) is used as a sequence for targeting localization in centromere; human histone H2B (full-length) for targeting localization in chromosome; a myristoylation signal from c-src (Non Patent Literature 13) for targeting localization in cytoplasmic membrane; and the N-terminal sorting signal of Tom70p (Non Patent Literature 14) for targeting localization in mitochondria. Any sequence may be used as long as it is known in the art and it induces localization within a cell.

The fusion protein, which is prepared by sandwiching a separase cleavage site between two types of fluorescent proteins different in wavelength and further fusing a localization-targeting sequence, as described above, is integrated in an expression vector such that two proteins falls in-frame. In this manner, the sensor is designed such that the fusion protein can be expressed within the cell. As the vector used herein, pIRESpuro2 (manufactured by Invitrogen) is used; however, any vector may be used as long as it can be efficiently expressed within a cell.

As the two types of fluorescent substances, fluorescent dyes such as FITC and Alexa 594 can be used; however, in consideration of expression within a cell, it is preferable to construct the sensor as a fusion protein by fusing a fluorescent protein. As the two types of fluorescent proteins, any fluorescent proteins may be used as long as they are known in the art and different in wavelength.

(Analysis Method)

Now, analysis using the separase sensor of the present invention and a method used in connection with analysis will be described below.

1. Image Analysis

Cells were seeded in a Lab-Tek chambered slide system (manufactured by NUNC) using $CO_2$-independent medium without phenol red (manufactured by GIBCO). The chamber lids were sealed with silicon grease and then put in use.

An image was observed by an inverted microscope (IX-71; manufactured by Olympus Corporation) using a Plan Apochromat oil objective lens (1003/1.40 NA) and recorded every 10 s, with 50 ms exposure time by a CoolSNAP HQ CCD camera (manufactured by Photometrics). Data of the obtained image was analyzed by ImageJ software (NIH).

Regions of centromeres (CENP-B) and chromosomes (histone H2B) were determined in the mCherry channel by thresholding. After the regions are determined, the mean fluorescence intensity of each of the regions is normalized to the value at time point −350 s before anaphase onset ($I^{EGFP}$ or $I^{mCherry}$, respectively).

The $R_{cut}$ values from each time point were obtained in accordance with the following expression and plotted to form a graph.

$$R_{cut}=1-I^{EGFP}/I^{mCherry}$$

Curves are fitted for $R_{cut}$ values of each experiment, and times when the curve cross the 50% of the $R_{cut}$ at the anaphase onset is defined as $T_{50}$.

2. Immunoprecipitation

Cells were lysed in a solution prepared by adding 100 nM okadaic acid and 0.25 U/L benzonase nuclease (manufactured by Novagen) to IP buffer (20 mM Tris-HCl, pH7.5, 150 mM sodium chloride, 20 mM β-glycerophosphoric acid, 50 mM magnesium chloride, 0.1% NP-40, protease inhibitor cocktail (Complete Mini EDTA-free, manufactured by Roche), 1 mM DTT) for 20 min on ice.

The resultant cell extracts, after removing the insoluble by centrifugation at 15,000 rpm for 30 min at 4° C., were used for immunoprecipitation.

Typically, the cell extracts are mixed with 10 IA of agarose beads conjugated to anti-myc tag (manufactured by MBL), or protein A beads (manufactured by Bio-RAD) coupled to the desired antibodies, and incubated for 2 hr at 4° C., then washed three times with IP buffer and three times with TBS-T (150 mM sodium chloride, 20 mM Tris pH 8.0, 0.05% (v/v) Tween 20) and then subjected to analysis.

3. Synchronisms of Cell Cycles and Chromosome Spreads

To obtain synchronous cell population traversing the transition from metaphase to anaphase, logarithmically proliferating HeLa cells are treated with 100 μM monastrol (manufactured by Tocris Biosciences) for 12 hr. Cells in the mitotic period were collected and treated with 5 μM ZM447439 (manufactured by Tocris Biosciences) for a predetermined time and collected for subjecting them to immunoprecipitation or size exclusion analysis.

4. Size-Exclusion Chromatography

The collected cells were washed twice with ice-cold PBS and snap-frozen in liquid nitrogen. The cells were resuspended in IP buffer supplemented with 100 nM okadaic acid and 0.25 U/L Benzonase nuclease (manufactured by Novagen), and incubated for 20 min on ice. Subsequently, the cells were centrifuged at 15,000×g for 10 min, filtered by an Ultrafree Centrifugal Filter unit (Ultrafree Centrifugal Filters, 0.45 μm, manufactured by Millipore) and fractionated by Superose 6 10/300 GL (manufactured by GE Healthcare). The column was run at a flow rate of 0.4 ml/min in IP buffer, and 250 μl fractions were collected.

5. Chromatin Fractionation

Nocodazole-arrested mitoric HeLa cells were collected by shake off. After washing with PBS, cells were lysed on ice 10 min in 10 mM HEPES (pH 7.9), 10 mM potassium chloride, 15 mM magnesium chloride, 0.34 M sucrose, 10% glycerol, 1 mM DTT, 0.25% Trioton X-100, and protease inhibitor cocktail (Complete Mini EDTA-free, manufactured by Roche). Chromosome-enriched fractions were collected by low-speed centrifugation at 1,300×g for 5 min and were washed twice with the above buffer.

6. Histone H1 Kinase Assay

After extensive washing, immunoprecipitated samples were put in IP buffer supplemented with 100 nM okadaic acid, 0.1 mg/ml histone H1 (manufactured by Roche), 80 nM ATP (pH 7.5), and 10 μCi [γ$^{32}$P] ATP and incubated for 20 min at room temperature. The reaction was stopped by the addition of SDS sample buffer, and phosphorylated substrates were detected by SDS-PAGE and autoradiography.

Example 2

(Analysis of Intracellular Localization of Separase by Separase Sensor)

Figure 2A:
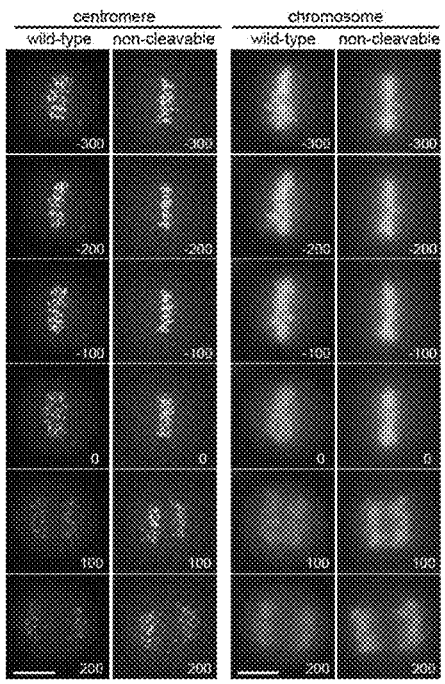
FIG. 2A shows static images taken at every 100 seconds of the activation of separase in centromere and chromosome, respectively, in mitotic living cells using wild-type and non-cleavable sensors in Example 2.

The results obtained by use of the separase sensor of the present invention are shown below. As the localization-targeting sequences, CENP-B and histone H2B are used and the sensor is localized respectively in centromere and the entire chromosome (FIG. 2A).

A separase sensor, which has 142nd-467th amino acids of a wild-type Scc1 containing a site to be cleaved with separase or a separase sensor, which has a non-cleavable site obtained by replacing arginine and glutamic acid, is introduced into a cell. Localization and activation of separase, which are observed in a mitotic living cell are shown in FIG. 2. Static images taken at every 100 seconds are shown (onset of anaphase is represented by 0).

It is observed that a separase sensor having CENP-B as a localization-targeting sequence and designed so as to localize in centromere, is localized in centromere and a separase sensor having histone H2B as a localization-targeting sequence and designed so as to localize in chromosome, is localized in chromosome.

If the fusion protein is not cleaved at a separase cleavage site, two fluorophores are co-localized and color tone exhibited by the mixture of two fluorescence colors is observed. Since EGFP emitting green fluorescence and mCherry emitting red fluorescence are used herein, the sensor before cleaved is expressed by yellow, which is a mixture of green and red converged on the image.

When separase is activated, an Scc1 peptide (pseudo substrate) is cleaved and two fluorescent proteins are separated. Since the red fluorophore is fused with a localization-targeting sequence, it remains in centromere or chromosome. In contrast, since the green fluorophore (EGFP) is cleaved in the Scc1 peptide, disintegrated from the localization-targeting sequence and disappear from centromere or chromosome. Accordingly, yellow signal changes to red.

When a non-cleavable sensor is used, extinction of green fluorescence, in other words, a color change from yellow to red fluorescence, is not observed (in FIG. 2A, which is a black and white photograph, since red color has dark tone, a color change from yellow to red occurring in a wild-type sensor is observed as extinction of fluorescence. In contrast, in the non-cleavable sensor, more specifically, both in non-cleavable sensors localized in centromere and chromosome, extinction of fluorescence is not observed at time points of 0, 100 or 200 seconds, unlike the wild-type sensor). In contrast, in the sensor having a wild-type Scc1 sequence, which is cleavable with separase, the color tone of the sensor changes from yellow to red at the onset (time-point of 0) of anaphase (in FIG. 2A, since red color has dark tone, extinction of fluorescence is observed; however, actually red fluorescence is emitted). The color-tone change is not observed also when separase is depleted by RNAi.

Using the separase sensor of the present invention, it was elucidated that activation of separase is observed not only at centromeres, where cohesin as a substrate is most abundant, but also along the entire lengths of mitotic chromosomes. Activation of separase occurs simultaneously and evenly on all over the chromosomes (FIG. 2A).

To quantitatively determine which sensor of those positioned in different sites is cleaved during a predetermined period in anaphase, fluorescent intensities of EGFP and mCherry on centromeres and chromosomes were measured and the parameter $R_{cut}$ was calculated. The parameter $R_{cut}$ is calculated in accordance with the expression:

$$R_{cut}=1-I^{EGFP}/I^{mCherry}.$$

Figure 2B:
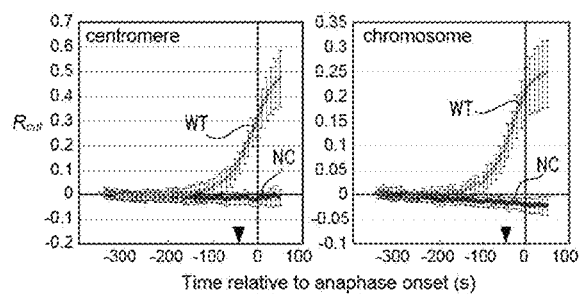
FIG. 2B are graphs showing $R_{cut}$ as a function of time relative to anaphase onset for wild-type and non-cleavable sensors in centromere and chromosome, respectively, in Example 2.

$R_{cut}$ reflects the cumulative ratio of Scc1 peptide cleaved by separase activity. Wild-type and non-cleavable Scc1 sensors are applied to a plurality of cells. Based on the observation results, $R_{cut}$ was analyzed. The results are shown in FIG. 2B. In the figure, arrow heads represent $T_{50}$ (described later).

The quantitative analysis results revealed that activation of separase is suppressed during much of metaphase until it becomes active shortly before anaphase onset. To provide an index for the timing of separase activation with respect to the point where chromosome segregation, a time point of activation, $T_{50}$, was determined. $T_{50}$ is defined as a point where an $R_{cut}$ value has progressed beyond 50% of the $R_{cut}$ at anaphase onset.

Figure 2C:
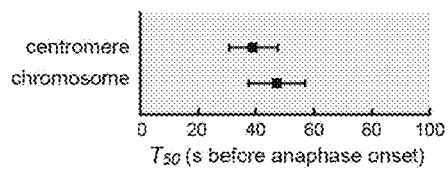
FIG. 2C is a graph showing a mean time point of activation, $T_{50}$, for centromere and chromosome in Example 2.

The mean $T_{50}$ value of the sensors localized in centromere was 39.0 s (±8.4 s, n=12) before anaphase onset; whereas the mean $T_{50}$ value of the sensors localized in chromosome was 47.2 s (±9.7 s, n=16) (FIG. 2C).

Figure 2D:
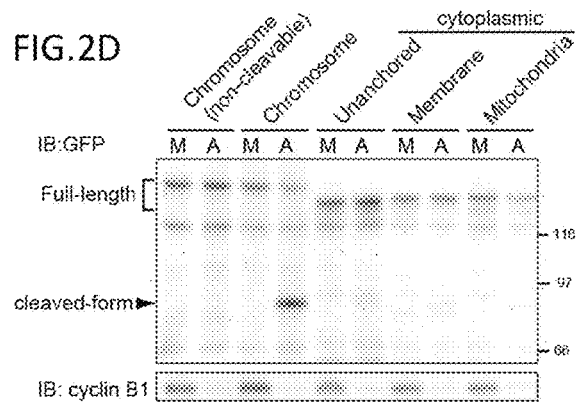
FIG. 2D shows an immunoblot as described in Example 2.

To analyze whether activation of separase occurs in the cytoplasm, sensors having targeting sequence to mitochondria, or cytoplasmic membrane and a sensor not having localization-targeting sequence was prepared. Localization of the sensor was observed by a fluorescence microscope and biochemical analysis was performed (FIG. 2D).

Sensors having a localization-targeting sequence targeting chromosome (Chromosome), cytoplasm (Unanchored), cytoplasmic membrane (Membrane) and mitochondria (Mitochondria) and a non-cleavable sensor having a chromosome localization-targeting sequence were expressed in cells. The cell was subjected to synchronized culture. The resultant cell extract was subjected to immunoblot with a anti-GFP antibody. As is confirmed by expression of cyclin B1, the cells are synchronized. In FIG. 2D, M represents metaphase and A represents anaphase.

The separase sensor localized in chromosome in the cells in anaphase is cleaved; however in other sites of a cell, a cleaved separase sensor, can be detected but only slightly, even if the cell is in anaphase. This shows that most of separase activation occurs in chromosome.

In consideration that chromosome-bound cohesin is a preferential substrate (Non Patent Literature 15) and in-vitro results that cleavage of cohesin is enhanced in the presence of DNA (Non Patent Literature 16), it is suggested that the sequence of pseudo substrate within the sensor of the present invention is cleaved in an analogous manner to that of endogenous cohesin.

The present invention makes it possible to not only visualize activation of separase but also quantitatively determine activation of separase by use of $R_{cut}$ and $T_{50}$.

Binding of Securin to Separase During Metaphase, Inhibition of Separase Activity, and Verification of the Results Obtained by Separase Sensor by a Biochemical Approach As described above, the activation of separase is suppressed during much of metaphase. Then, to elucidate its mechanism, the following experiment was performed.

Figure 3A:
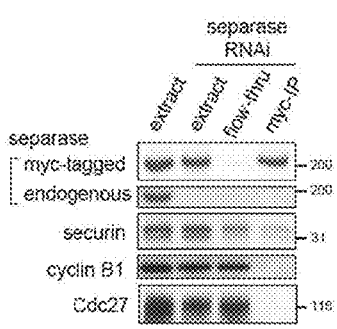
FIG. 3A shows the result of an immunoprecipitation assay described in Example 2.

FIG. 3A shows the results of immunoprecipitation assay using spindle assembly checkpoint (SAC)-arrested cell extract. HeLa cells with myc-tag and expressing separase were treated with RNAi to deplete endogenous separase (separase RNAi) and treated with nocodazole to arrest cell division at metaphase. The cells were subjected to immunoprecipitation with an anti-myc antibody. As a control, cells having endogenous separase (not depleted with RNAi) were used.

A cell extract (extract), an unbound fraction (flow-thru) and a bound fraction to anti-myc antibody (myc-IP) were analyzed by immunoblot for the presence or absence of the proteins shown in the left-hand of FIG. 3A. As a result, it was found that even after the fraction having separase binding is removed from the extract, a considerable amount of securin is present (see FIG. 3A, "flow-thru"). This is considered because the amount of securin exceeds the amount of separase in the HeLa cell.

Furthermore, proteins bound to separase were analyzed by size-exclusion chromatography.

Figure 3B:
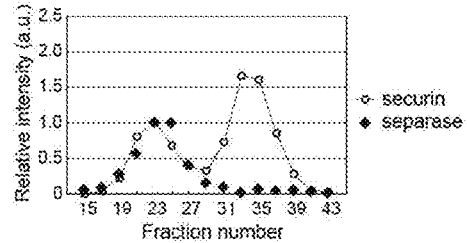
FIG. 3B shows an immunoblot as described in Example 2.

The SAC-arrested cell extract was treated with nocodazole and subjected to gel filtration. The presence or absence of separase, securin and cyclin B1 in each fraction was analyzed by immunoblot. The results are shown in FIG. 3B. Relative protein amounts of individual fractions are normalized based on that of fraction 23 and shown in FIG. 3C. It was elucidated that an extremely small amount of securin alone is fractionated together with separase near a molecular weight of 500 kDa and a most part of securin is present in a fraction where no binding to separase was observed (FIG. 3B, 3C).

The surplus amount of securin over separase may prevent activation of separase as soon as APC/C activates. In order to biochemically verify this, it is necessary to obtain a cell population that progressed synchronously from metaphase to anaphase.

As a result of research on many protocols for obtaining synchronized cells, the present inventors found that the release of SAC-arrested cells by inhibiting Aurora B (Non Patent Literatures 17, 18) provided the best synchronous population to transit from metaphase to anaphase.

Figure 3D:
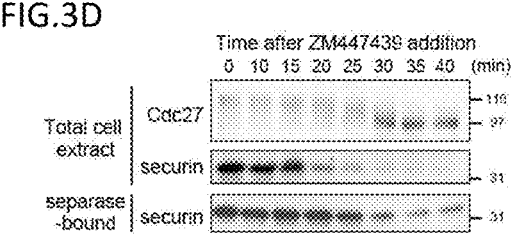
FIG. 3D shows an immunoprecipitation assay as described in Example 2.
Figure 3E:
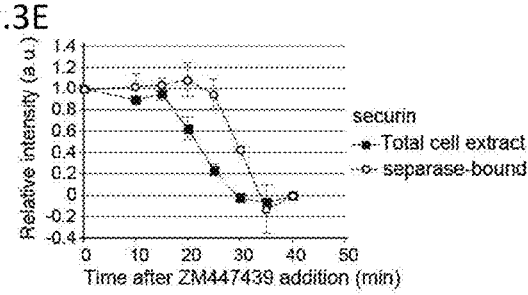
FIG. 3E is a graph showing relative protein amounts of individual fractions as described in Example 2.

Ten minute later SAC-arrested cells were treated with an Aurora B inhibitor, i.e., ZM447439, to release checkpoint, collection of a sample was started at the time intervals of 5 minutes. A cell extract (total cell extract) and a separase-bound fraction were analyzed for the presence or absence of Cdc27 and securin by immunoblot. The results of the immunoblot are shown in FIG. 3D and the results quantitatively analyzed are shown in FIG. 3E. It was found that twenty minutes after addition of the Aurora B inhibitor (ZM447439), the amount of securin in extracts began to decline and dropped to a basal level after 30 min.

However, the amount of separase-bound securin remained unchanged and began to decline only after 30 min, when the majority of the cells entered anaphase, as indicated by the reversal of the upshift of Cdc27. In FIG. 3D, electrophoretic mobility of Cdc27 changes. This indicates that a cell population transited to an anaphase-like state (FIGS. 3D, 3E).

Figure 3F:
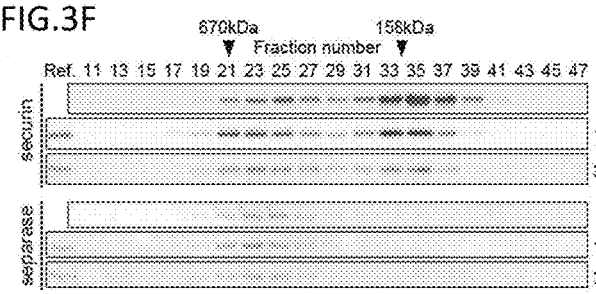
FIG. 3F shows an immunoblot as described in Example 2.
Figure 3G:
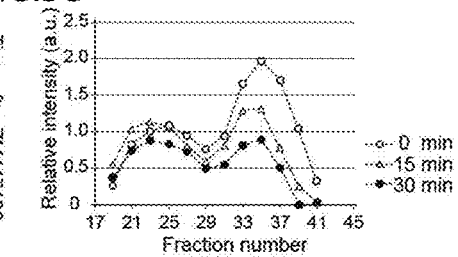
FIG. 3G is a graph showing a relative change in securin in Example 2.

The results of gel filtration analysis are also consistent with the above results (FIGS. 3F, 3G). At the time points of 0, 15 and 30 minutes after addition of ZM447439, cells were taken and a cell extract was prepared and subjected to gel filtration. The presence of securin and separase in individual fractions was analyzed by immunoblot. The results of the immunoblot are shown in FIG. 3F and a relative change in amount of securin is shown in FIG. 3G. Securin observed around a molecular weight of 150 kDa, which is not fractionated together with separase, reduces in amount in the first place; whereas the amount of securin observed around a molecular weight of 500 kDa, which is fractionated together with separase is almost unchanged during the time of the analysis.

Thus, a predetermined amount of securin persistently binds separase throughout much of metaphase in the presence of APC/C activity and inhibits activation of separase. This might be because separase-free securin serves as a better substrate for the APC/C-mediated proteolysis or because a high binding affinity of securin to separase maintains a fraction of securin bound to separase.

Example 3

(Physiological Relevance of Cyclin B1 Binding to Separase Before Anaphase)

The persistent binding of securin to separase would explain how separase remains inactive during much of metaphase. However, there are a number of observations that question the significance of securin in regulating separase activity in mammalian cells (Non Patent Literatures 19-22).

An alternative regulation pathway for suppressing separase activity is through an interaction with cyclin B1, which depends on the phosphorylation of Ser1126 residue in human separase (Non Patent Literatures 23, 24).

Despite the biochemical evidence for cyclin B1 having the ability to inhibit separase, its role of cyclin B1 in preventing chromosomal segregation has been demonstrated only conditionally (Non Patent Literatures 25, 26). The present inventors observed that the bulk of cyclin B1 did not cofractionate with separase in a SAC-arrested cell extract (FIG. 3B), discounting the significance of inhibitory activity of cyclin B1 before anaphase.

Figure 4A:
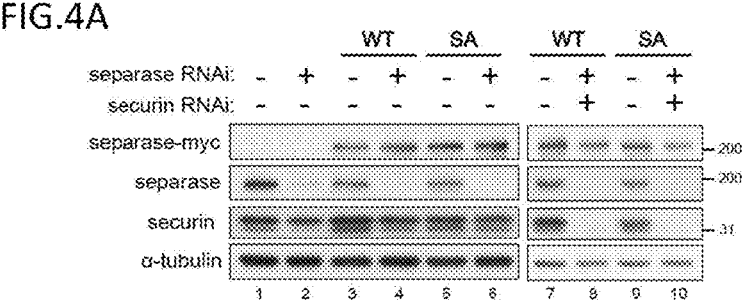
FIG. 4A shows an immunoblot of HeLa cells expressing wild type (WT) or alanine mutant of serine1121 (SA) of mouse separase as described in Example 3.

With the use of our the separase sensor of the present invention, the present inventors sought to reinvestigate the role of cyclin B1 in controlling the proteolytic activity of separase. To do this, the present inventors generated HeLa cells that stably express myc-tagged mouse separase bearing an alanine mutant at serine 1121 (SA). A serine 1121 (SA) mutant (hereinafter referred to as an SA mutant) of separase abolishes the binding ability to cyclin B1. Furthermore, HeLa cells expressing wild-type (WT) separase were generated as a control and used in analysis. Separase and securin expressed in the cells thus prepared are shown in FIG. 4A.

To obtain expression at a physiological level, a gene introduction technique based on a bacterial artificial chromosome (BAC) (Non Patent Literature 27) is used. Expression cells for a wild-type (WT) and alanine-replaced mutant (SA) were treated with RNAi to deplete endogenous separase and securin. In these cell strains, the cells treated with RNAi to deplete endogenous separase express myc-tagged mouse separase, in place (see FIG. 4A, lanes 4 and 6).

Although data were not shown herein, in cells having a substitution with wild-type mouse separase, cell division occurs equivalently. From this, it was shown that mouse separase is functional in human cells. Furthermore, it was confirmed that wild-type separase binds to cyclin B1 more efficiently in the absence of securin. This is consistent with the results shown before (Non Patent Literature 24). It was also confirmed that SA separase lacks binding ability, irrespective of the level of securin.

Figure 4B:
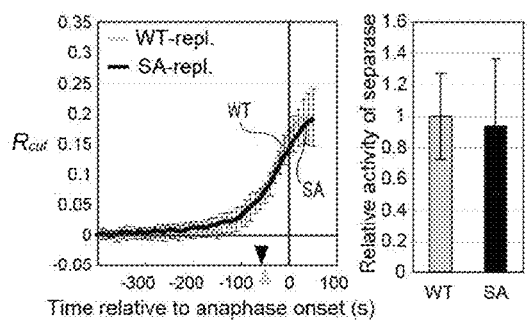
FIG. 4B are graphs showing $R_{cut}$ as a function of time relative to anaphase onset (left panel) and relative activity of separase (right panel) using HeLe cells in which endogenous separase was replaced with WT or SA mutant of mouse separase as described in Example 3.

Activation of separase was analyzed by using HeLa cells in which endogenous separase was replaced with the above wild-type mouse separase or SA mutant mouse separase, and by use of the separase sensor of the present invention. Using wild-type mouse separase replaced cell (WT-repl.) and SA mutant mouse separase replaced cell (SA-repl.), activation of separase was analyzed based on static images of living cells in the same manner as in FIG. 2A and $R_{cut}$ values were calculated. The results are shown in FIG. 4B (left). FIG. 4B (right) shows relative activity of separase at onset of anaphase. It was elucidated that even in a SA mutant mouse separase replaced cell, kinetics of separase activation are almost the same as that in a wild-type mouse separase replaced cell.

Figure 4C:
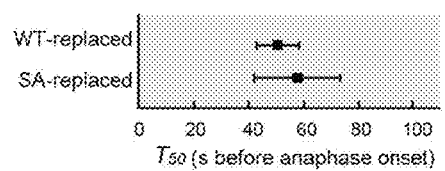
FIG. 4C is a graph showing a mean time point of activation, $T_{50}$ for HeLa cells replaced with WT or SA mutant of mouse separase as described in Example 3.

The activity of separase is conceivably reflected by first derivation of $R_{cut}$; however, both in cells replaced with a wild-type separase and an SA mutant mouse separase, separase activity levels of them are equivalent, as shown in FIG. 4B (right). In addition, $T_{50}$ values of them are also equivalent (FIG. 4C).

These results support that the binding of cyclin B1 to separase is dispensable for separase regulation prior to anaphase.

Subsequently, securin and separase were both inactivated and function in regulating separase was analyzed. To describe more specifically, in an SA mutant mouse separase replaced cell, both mechanisms were inactivated by depleting securin with RNAi (FIG. 4A, lanes 8 and 10).

Figure 4D:
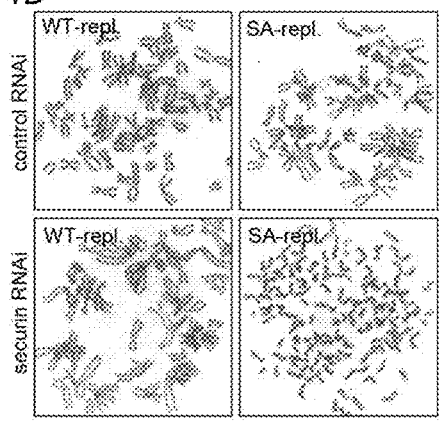
FIG. 4D shows microscopic images of chromosomes stained with Giemsa solution as described in Example 3.

An SA mutant mouse separase replaced cell (SA-repl.) and a wild-type mouse separase replaced cell (WT-repl.) were treated with RNAi to deplete securin (securin RNAi), and treated with nocodazole for 12 hours. Cells in mitotic period were collected and chromosomes were spread out, stained with Giemsa and subjected to analysis. In the cells treated with nocodazole, sister chromatids are separated and dispersed in the cytoplasm (FIG. 4D). In about 80% of securin-depleted SA mutant mouse separase replaced cells, mispairing of chromosomes occurs; however, the percentage of other cells in which such mispairing is observed is only about 5% or less.

Furthermore, using cells not treated with nocodazole, roles of securin and separase were analyzed in cell division. HeLa cells (parent strain), SA mutant mouse separase replaced cell (SA-repl.) and wild-type mouse separase replaced cell (WT-repl.) were treated with RNAi to suppress securin expression for 24 hours. Images of about 50 living cells in the period of cell division were analyzed. The case where all paired sister chromatids are simultaneously separated is denoted by "normal anaphase"; the case where chromatids are separated at random during continuous mitotic division is denoted by "premature disjunction", and the case classified in neither one of them is denoted by "unclassified" (FIG. 4E).

Figure 4E:
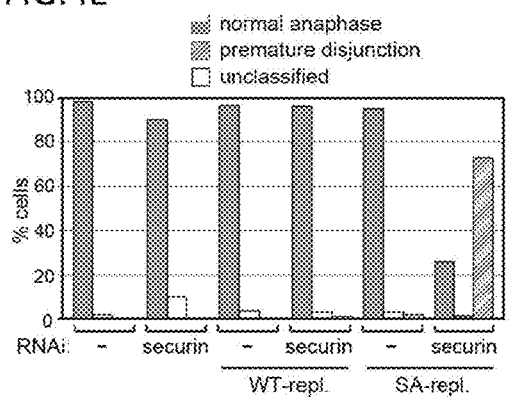
FIG. 4E is a graph showing results of live-cell imaging analysis from Example 3.

As a result, in most of the securin-depleted SA mutant replaced cells, it was found that sister chromatids are prematurely separated during prolonged metaphase (FIG. 4E).

Such premature disjunction is rarely observed in wild-type separase replaced and securin-depleted cells serving as a control.

Example 4

(Securin and Cyclin B1 not Only Suppress Separase Activity but Also Act in Localization in Chromosome)

In the wild-type mouse separase replaced cell (WT-repl.), SA mutant mouse separase cell (SA-repl.), securin was depleted and activation of separase was analyzed. Histone 2B was used as a localization-targeting sequence and activation of separase was analyzed by use of a separase sensor localized in chromosome (FIGS. 5A, 5B).

Figure 5A:
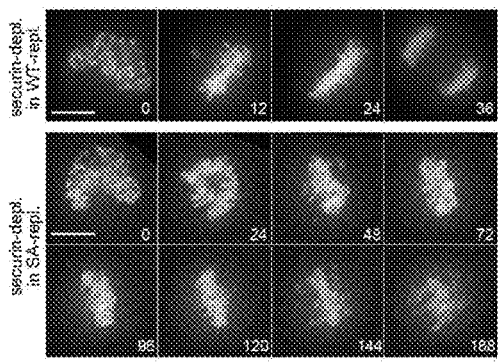
FIG. 5A shows static images of living cells during mitosis as described in Example 4.

FIG. 5A shows image analysis of living cells, more specifically, arrangement of static images of cells during mitosis chronologically from nuclear envelope breakdown (NEBD). In the securin-depleted SA mutant mouse separase replaced cells, metaphase is prolonged and sister chromatids are separated at random.

From the above analysis of the experiment using a separase sensor, $R_{cut}$ values were obtained and plotted with time (NEBD was determined as a time point of 0). Compared to the securin-depleted wild-type mouse separase replaced cell (WT-repl.), in the securin-depleted SA mutant mouse separase replaced cell (SA-repl.), the activity of separase is high but only very slightly.

Figure 5B:
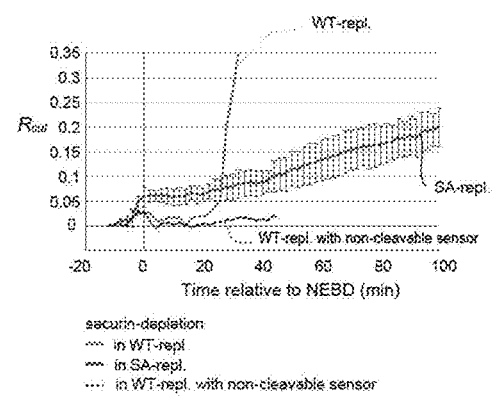
FIG. 5B is a graph showing $R_{cut}$ as a function of time relative to NEBD as described in Example 4

In these securin-depleted SA mutant mouse separase replaced cell (SA), instead of being completely inactivated through metaphase, the $R_{cut}$ value followed linear increase from nuclear envelope breakdown (FIG. 5B). This means that a certain level of separase activity is detected on chromosomes as soon as the nuclear envelope disintegrated. Based on these observations, it is found that separase is constitutively activated when it does not bind to securin or cyclin B1, but its activation level remains low.

From the above results, it is suggested that separase must be bound to securin or cyclin B1 for activating separase in chromosome.

Figure 5C:
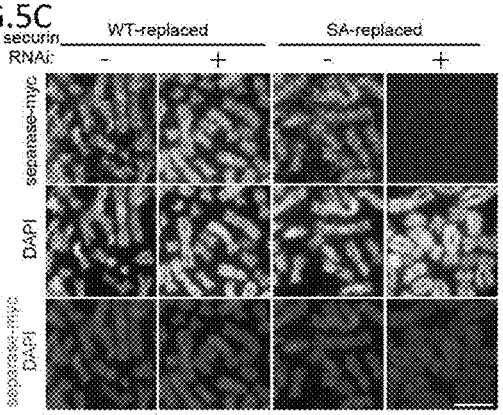
FIG. 5C shows images of chromosomal localization of separase as described in Example 4.

In the wild-type mouse separase replaced cell (WT-replaced) and SA mutant mouse separase cell (SA-replaced), myc-tagged separase was expressed and stained with an anti-myc antibody. In this manner, localization of separase was analyzed. It is reported that in the mitotic phase, a separase fraction is localized in chromosome (Non Patent Literature 16). In addition, the present inventors found that separase cannot be localized in chromosome under the condition that separase cannot be bound to securin or cyclin B1 (FIG. 5C).

Figure 5D:
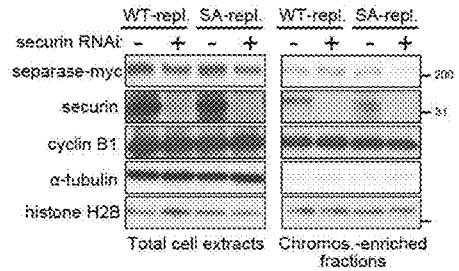
FIG. 5D shows an immunoblot as described in Example 4.

The above results were biochemically analyzed (FIG. 5D). The wild-type mouse separase replaced cell (WT-repl.) and SA mutant mouse separase cell (SA-repl.) expressing myc-tagged separase, were treated with RNAi to deplete securin, and treated with nocodazole. In this manner cells in the mitotic period were collected to prepare cell extracts. In cell extracts (Total cell extracts) and chromosome enriched fractions (Chroms.-enriched fractions), expression levels of myc-tagged separase, securin and cyclin B1 were analyzed by immunoblot. Note that α-tubulin and histone H2B were used in the analysis in order to indicate that the amounts of proteins are almost equivalent.

Consistent with the results of microscope analysis, in chromosome fractionation analysis, although the amount of separase in the cell extract from securin-depleted SA mouse separase mutant replaced cells was rarely changed, a decrease in amount of separase was observed in the chromatin enriched fraction. These results suggest that chromosomal localization of separase depends on securin or cyclin B1.

The finding that depletion of securin causes premature separase activation and chromosome disjunction in SA mutant replaced cells is consistent with the proposed idea that cyclin B1 can bind separase and restrain its precocious activation before anaphase (Non Patent Literatures 25, 26).

Figure 6A:
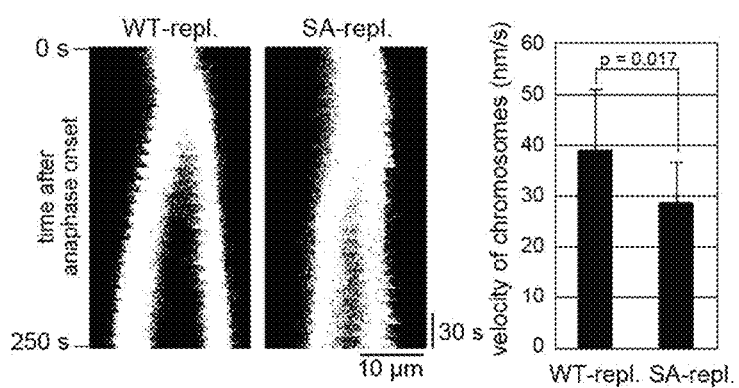
FIG. 6A shows kymographs of typical separation of sister chromatids (left panel) and velocity of chromosomes (right panel) as discussed in Example 4.

However, the present inventors found that in the SA mutant replaced cell, even if anaphase is completed, failed to carry out the rapid movement of unpaired sister chromatids toward opposite poles, and sisters stayed in the vicinity of the equatorial plate for a longer periods of time. FIG. 6A shows kymographs of typical separation of sister chromatids. Time-lapse motion images of a cell expressing H2B-mCherry were taken at the intervals of 10 seconds after onset of anaphase. Of these images, images of the equatorial plane during the mitotic period are chosen and chronologically arranged. The bar along the vertical axis indicates 30 seconds; whereas the bar along the transverse axis indicates 10 m. The velocity of poleward movement of a separated sister chromatid was determined from the image taken above and indicated in FIG. 6A (right graph). The mean velocity of movement of the sister chromatid in the wild-type mouse separase replaced cell was 39.0±12.2 nm/s and that of the SA mutant mouse separase replaced cell was 28.6±8.3 nm/s (t test, p=0.017).

The above results prompts us to analyze the interaction between separase and cyclin B1 in anaphase in the same manner as in FIG. 3D. The interaction between securin and cyclin B1 in metaphase-to-anaphase transition time was analyzed by immunoblot (FIGS. 6B, 6C).

The cells were treated with Monastrol and a checkpoint was released by Aurora B inhibitor. From this time point, the cells were collected at the time intervals of 5 minutes. From the cell population, which transits toward anaphase, a cell extract was obtained. The total cell extract (TCE) and a separase-bound fraction (separase-bound) were subjected to immunoblot. Behaviors of myc-tagged separase, securin and cyclin B1 were analyzed.

Figure 6B:
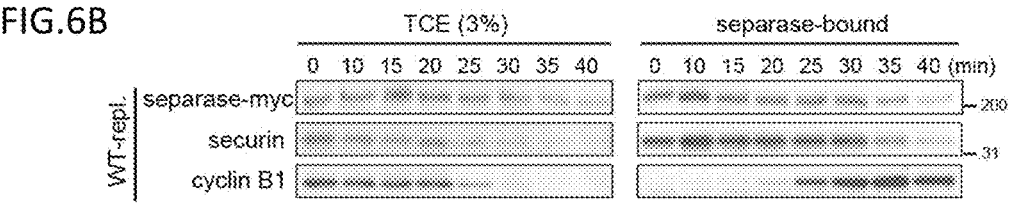
FIG. 6B shows an immunoblot as described in Example 4.
Figure 6C:
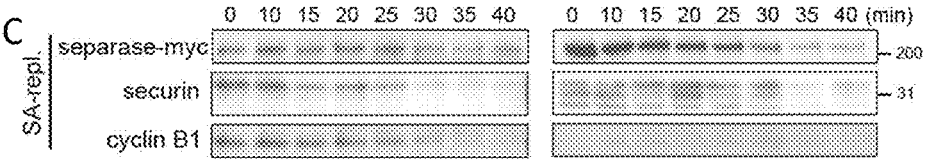
FIG. 6C shows an immunoblot as described in Example 4.

As a result, it was found that cyclin B1 coprecipitates with separase at later time points during M/A transition (FIG. 6B). Binding of cyclin B1 to separase was abolished in a 1121 (serine to alanine) mutant, i.e., SA mutant replaced cell, suggesting that the rapid poleward movement of chromosome was related to separase's inability to associate with cyclin B1 in anaphase (FIG. 6C). Therefore, although the binding of cyclin B1 to separase is dispensable in metaphase, it seems to become relevant in anaphase.

Figure 7A:
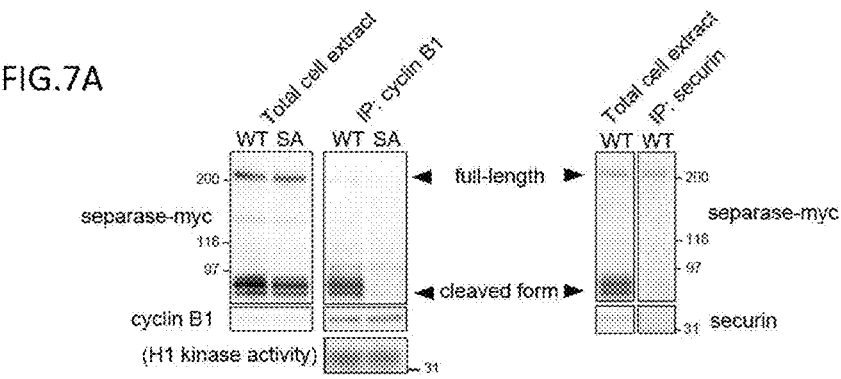
FIG. 7A shows shows an immunoblot as described in Example 4.

Furthermore, in immunoprecipitation experiment, it was found that securin binds to full-length separase, whereas cyclin B1 binds to cleaved separase in an extract of cells in anaphase (FIG. 7A).

In the wild-type mouse separase replaced cell and SA mutant mouse separase replaced cell, the cell cycle arrest by Monastrol, was cancelled. Forty minutes after cancellation of the cell cycle arrest by Monastrol a cell population enriched in anaphase cells was prepared. Then, a cell extract was obtained and subjected to immunoprecipitation with cyclin B1 and securin to analyze the presence or absence of separase-myc. As a result, separase having a small molecular weight, i.e., cleaved separase, is observed. Because the cleaved separase is generated by its own proteolytic activity (Non Patent Literatures 28, 29), these results imply that binding to cyclin B1 occurs after separase is activated.

To study whether separase inhibits cdk1 in anaphase, cyclin B1-associated cdk1 activity was measured, and asked whether the activity of cdk1 declines in anaphase of SA mutant replaced cells.

Contrary to our expectations, no difference in the cdk1 activity was observed between the SA mutant replaced cell and the wild-type replaced cell against expectation when cyclin B1 was immunoprecipitated from the cell extracts of cell populations enriched in anaphase cell, (FIG. 7A, lower left, H1 kinase activity).

Figure 7B:
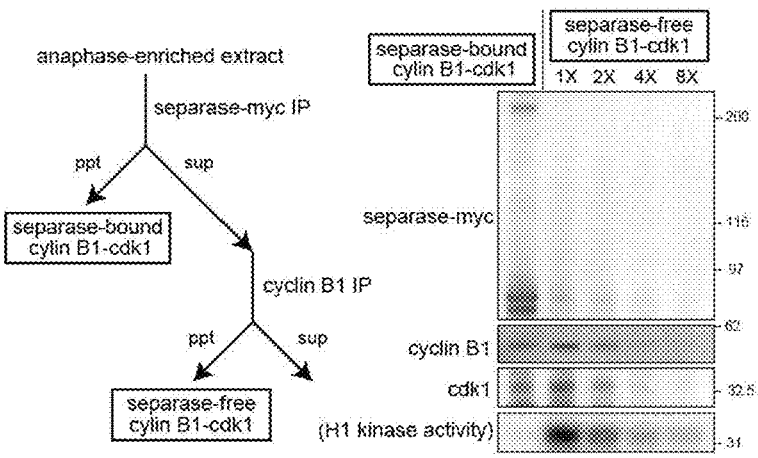
FIG. 7B shows a diagram of preparation for separase-bound or separase-free cyclin B1-cdk complex fraction (left panel) and an immunoblot (right panel) as described in Example 4.

However, a fraction in which a cyclin B1-cdk1 complex binds to separase was prepared and compared to a fraction in which the complex did not bind to separase, it was elucidated that cdk1 activity was markedly inhibited in the separase-bound fraction (FIG. 7B).

A cell population containing a large number of anaphase cells was prepared from wild-type mouse separase replaced cells, and subjected to immunoprecipitation with a separase antibody. A separase-bound cyclin B1-cdk1 fraction and a separase-free cyclin B1-cdk1 fraction were analyzed for the amounts of cyclin B1 and cdk1 contained in the fractions and the activity of kinase to histone H1 as a substrate. The results are shown in FIG. 7B (right).

In these experiments, it was found that a detectable amount of cyclin B1-cdk1 is present and kinase activity is present even after removing the separase-bound fraction from the extract (FIG. 7B; separase-free cyclin B1-cdk1). It was also found that, in the separase-bound fraction, kinase activity is inhibited (separase-bound cyclin B1-cdk1).

In the extract enriched in anaphase cells was concentrated, the bulk of cyclin B1 had already been degraded, separase binds to a part of cyclin B1 and inhibits the cdk1 activity.

Figure 7C:
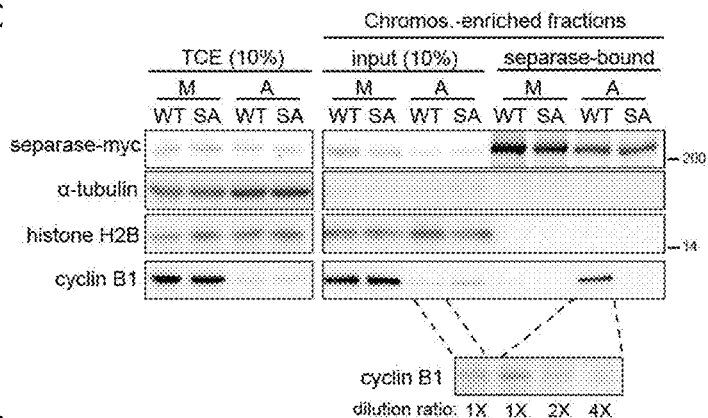
FIG. 7C shows an immunoblot as described in Example 4.

From wild-type mouse separase replaced cells (WT) and SA mutant mouse separase replaced cells (SA) in metaphase (M) and anaphase (A), chromosomes were concentrated to collect fractions (chromos-enriched fractions), subjected to immunoprecipitation with an anti-myc antibody and analyzed by immunoblot. The analysis results are shown in FIG. 7C in which TCE represents a total cell extract.

Remarkably, a significant amount of separase-bound cyclin B1 in chromosome-enriched fraction prepared from an anaphase population was detected. It is estimated that more than 20% of cyclin B1 in immunoprecipitated cyclin B1 was bound to separase.

To verify these biochemical data in cell populations, which transit toward anaphase, the stability of cdk1-mediated phosphorylation of INCENP, specifically the threonine at position 59 (Thr59), was assessed. It has been known that the threonine at position 59 is dephosphorylated simultaneously upon the onset of anaphase (Non Patent Literature 30).

Figure 7D:
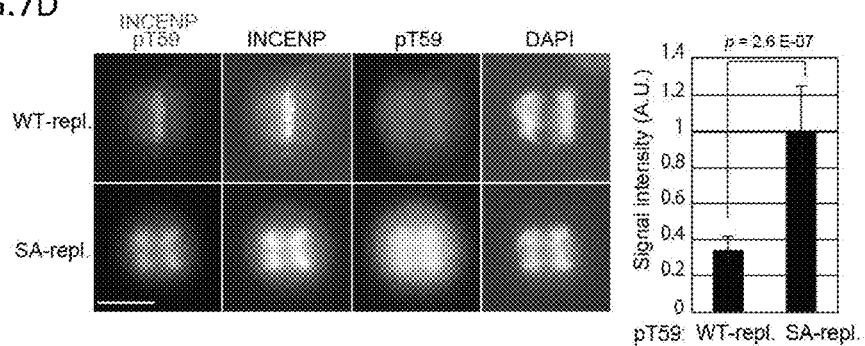
FIG. 7D shows images from a fluorescence microscope (left panel) and signal intensity of pT59 (right panel) as described in Example 4.

A wild-type mouse separase replaced cell (WT) and an SA mutant mouse separase replaced cell (SA) are immobilized, and stained with an INCENP antibody (INCENP), antibody (p59) capable of detecting phosphorylation of the threonine at position 59 of an INCENP and DAPI (FIG. 7D). Since DAPI stains DNA, anaphase cells where chromosomes are segregated are detected. As a result of observation by an immunofluorescence microscope, it was shown that INCENP Thr59 in chromosome of SA mutant mouse separase replaced cell remains phosphorylated during anaphase.

These results indicate that activated separase binds to and inhibits a cyclin B1-cdk1 complex including a cyclin B1-cdk1 fraction distributed in chromosome. In consideration that separase is activated in chromosome, a plausible possibility is that separase-mediated inhibition of cdk1 on chromosomes is required for the rapid poleward movement of sister chromatids.

Figure 8:
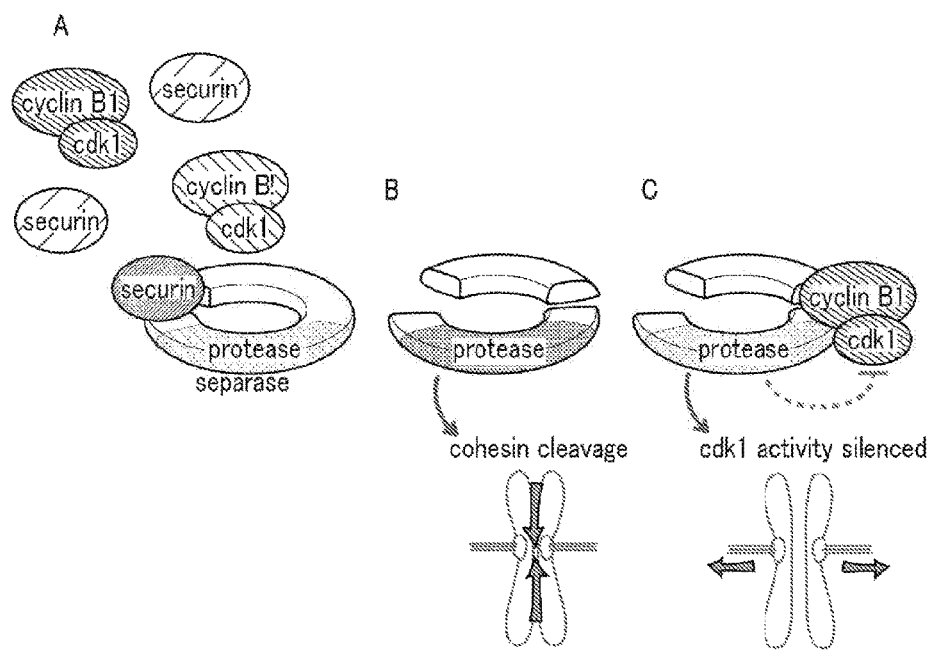
FIG. 8 shows a model of a control mechanism by separase in anaphase of cell division.

Based on the results obtained by use of the separase sensor and the results obtained by biochemical approach, FIG. 8 illustrates a model how separase, securin, cyclin B1 and cdk1 functionally interact with each other.

The present inventors successfully visualized activation of separase by use of a separase sensor. Since separase activity can be visualized by the separase sensor of the present invention, the timing of separase activation and localization of separase within a cell are clarified. Furthermore, not only visualization can be made but also kinetically analysis can be made based on the obtained results by the sensor of the present invention, with the result that separase activation can be quantitatively evaluated.

As is described in the above, since detailed mechanism of cell division can be analyzed by the separase sensor of the present invention, abnormal cell division, i.e., chromosomal instability and canceration mechanism can be analyzed, and furthermore, screening of anticancer agents can be also made.

The invention claimed is:

1. A biosensor for measuring and/or detecting separase activity in cultured cells, comprising:
   a first fluorescent substance at a first end of the fragment of human Scc1, said fragment consisting of the polypeptide of SEQ ID NO. 1;
   a second fluorescent substance at the second end of the fragment consisting of the polypeptide of SEQ ID NO. 1: and
   a localization-targeting sequence for localizing the biosensor at a localization site within the cultured cells, said localization-targeting sequence at the N- or C-terminus of the biosensor:
   wherein the localization-targeting sequence is not a sequence derived from Scc1;
   wherein the first fluorescent substance and the second fluorescent substance have non-overlapping emission wavelengths that do not cause excitation of each other; and
   wherein the biosensor is a separase sensor configured to detect and/or measure separase activity at the localization site within the cultured cells as a function of a change in emission fluorescence of the biosensor resulting from cleavage of the fragment consisting of the polypeptide of SEQ ID NO. 1 by separase.

2. The biosensor according to claim 1, wherein the first and the second fluorescent substances are fluorescent proteins.

3. The biosensor according to claim 2, wherein the localization-targeting sequence specifically localizes the biosensor at centromeres.

4. The biosensor according to claim 3, wherein the localization-targeting sequence for centromeres is CENP-B.

5. A method to visualize and analyze proteolytic activity of separase in the context of chromosomal segregation in living cells, by transfected vector-derived separase sensor according to claim 4.

6. A method for screening anticancer agents, comprising contacting test substances to the separase sensor according to claim 1, visualizing the separase activity, and screening anticancer agents based on separase activity as an index.

7. The biosensor according to claim 2, wherein the localization-targeting sequence specifically localizes the biosensor at chromosomes.

8. The biosensor according to claim 2, wherein the localization-targeting sequence specifically localizes the biosensor at cytoplasmic membrane.

9. The biosensor according to claim 2, wherein the localization-targeting sequence specifically localizes the biosensor at mitochondria.

10. The biosensor according to claim 7, wherein the localization-targeting sequence for chromosomes is histone H2B.

* * * * *